United States Patent [19]

Darbellay et al.

[11] Patent Number: 4,668,807

[45] Date of Patent: May 26, 1987

[54] PROCESS FOR REDUCING THE CONTENT OF HYDROLYZABLE CHLORINE IN GLYCIDYL COMPOUNDS

[75] Inventors: Jacques Darbellay, Muraz-Collombey; Gerald Dessauges, Montreux, both of Switzerland

[73] Assignee: Ciba-Geigy Corporation, Ardsley, N.Y.

[21] Appl. No.: 807,566

[22] Filed: Dec. 11, 1985

[30] Foreign Application Priority Data

Dec. 21, 1984 [CH] Switzerland .................... 6098/84

[51] Int. Cl.$^4$ .......................................... C07D 301/32
[52] U.S. Cl. .................................... 549/542; 544/221; 544/318; 548/309; 548/318; 525/507; 528/489
[58] Field of Search ................. 549/542; 525/507; 528/489; 544/221, 318; 548/309, 318

[56] References Cited

U.S. PATENT DOCUMENTS 4,017,523 4/1977 Vargiu et al.

FOREIGN PATENT DOCUMENTS 58-173116 10/1983 Japan .
1278737 6/1972 United Kingdom .

OTHER PUBLICATIONS

H. Lee and K. Neville, Handbook of Epoxy Resins, McGraw Hill, New York, 1967, pp. 4–30.

*Primary Examiner*—Norma S. Milestone
*Attorney, Agent, or Firm*—Luther A. R. Hall

[57] ABSTRACT

To reduce the content of hydrolyzable chlorine in glycidyl compounds, these are dissolved in a halogen-free organic solvent and treated with an equivalent excess of aqueous alkali metal hydroxide solution at elevated temperature, the excess being 100 to 200% of the equivalent amount theoretically required for complete dehydrochlorination of the hydrolyzable chlorine, the water is then removed from the organic solution, the organic solution is treated with 5 to 500 times the amount, based on the amount of alkali metal hydroxide employed, of moist cellulose containing up to 35% by weight of water at elevated temperature and, after filtration, the glycidyl compound is isolated from the organic solution.

11 Claims, No Drawings

PROCESS FOR REDUCING THE CONTENT OF HYDROLYZABLE CHLORINE IN GLYCIDYL COMPOUNDS

The present invention relates to a process for reducing the content of hydrolysable chlorine in glycidyl compounds by after-treatment thereof with excess alkali metal hydroxide and subsequent treatment with moist cellulose.

As is known, the glycidyl compounds prepared by means of epichlorohydrin, especially those prepared industrially, are always contaminated with chlorine, which is present in the epoxy resin as ionic chlorine and in the glycidyl compound as hydrolysable chlorine (1,2-chlorohydrin) and as non-hydrolysable chlorine (methyl chloride).

Higher requirements in respect of purity are continually being imposed on epoxy resins, especially those which are used for the production of electrical and electronic components, in order to reduce the corrosion influence of the residual chlorine content on substrates, in particular contact metals.

Many methods have already been disclosed for removing the residual chlorine content from epoxy resins. As documented in "Handbook of Epoxy Resins" (1967), 4–30, by H. Lee and K. Neville, these methods also have disadvantages.

Specific processes for the preparation of polyglycidyl ethers by two dehydrohalogenation reactions by means of sodium hydroxide solution are disclosed both in British Patent No. 1,278,737 and in German Offenlegungsschrift No. 2,523,696. The amount of total chlorine in the polyglycidyl ethers obtained according to the process is still relatively high. Japanese Preliminary Published Patent Application No. 58-173116 proposes removal of the residual chlorine content in epoxy resins by means of silver salts of organic acids. Apart from the fact that this is an expensive process, our own repeat work has shown that the effect achieved by this process is slight.

It has now been found that the content of hydrolysable chlorine in glycidyl compounds can be greatly reduced if these are treated in an organic solvent with an excess of alkali metal hydroxides at elevated temperature and then with moist cellulose at elevated temperature, the ionic chlorine formed during the dehydrochlorination also being largely removed from the epoxy resin composition. In the process according to the invention, it is not necessary to neutralise the excess alkali metal hydroxide in the reaction solution after the alkali metal hydroxide treatment or to remove it from the solution before the further treatment with moist cellulose.

The present invention thus relates to a process for reducing the content of hydrolysable chlorine in glycidyl compounds by after-treatment of the glycidyl compounds with alkali metal hydroxides, which comprises treating the glycidyl compound, dissolved in a halogen-free organic solvent, with an equivalent excess of an aqueous alkali metal hydroxide solution at elevated temperature, the excess being 100 to 200% of the equivalent amount theoretically required for complete dehydrochlorination of the hydrolysable chlorine, removing the water from the organic solution, treating the organic solution with 5 to 500 times the amount, based on the amount of alkali metal hydroxide employed, of moist cellulose containing up to 35% by weight of water at elevated temperature and, after filtration, isolating the glycidyl compound from the organic solution.

Glycidyl compounds which contain glycidyl groups bonded directly to oxygen, nitrogen or sulfur atoms can be employed in the process according to the invention. Examples of such resins are polyglycidyl and poly($\beta$-methyl-glycidyl)esters, which can be obtained by reacting a compound containing two or more carboxylic acid groups per molecule with epichlorohydrin, glycerol dichlorohydrin or $\beta$-methylepichlorohydrin in the presence of an alkali. Such polyglycidyl esters can be derived from aliphatic polycarboxylic acids, for example oxalic acid, succinic acid, glutaric acid, adipic acid, pimelic acid, suberic acid, azelaic acid, sebacic acid or dimerised or trimerised linoleic acid, from cycloaliphatic polycarboxylic acids, such as tetrahydrophthalic acid, 4-methyltetrahydrophthalic acid, hexahydrophthalic acid and 4-methylhexahydrophthalic acid, and from aromatic polycarboxylic acids, such as phthalic acid, isophthalic acid and terephthalic acid.

Further examples are polyglycidyl and poly($\beta$-methylglycidyl)ethers which can be obtained by reacting a compound containing at least two free alcoholic and/or phenolic hydroxyl groups per molecule with the corresponding epichlorohydrin under alkaline conditions, or in the presence of an acid catalyst with subsequent treatment with an alkali. These ethers can be prepared with the glycidylating agents mentioned, for example from acyclic alcohols, such as ethylene glycol, diethylene glycol, higher poly-(oxyethylene)glycols, propane-1,2-diol, poly-(oxy-propylene)glycols, propane-1,3-diol, poly-(oxytetramethylene)glycols, pentane-1,5-diol, hexane-2,4,6-triol, glycerol, 1,1,1-trimethylolpropane, pentaerythritol and sorbitol, from cycloaliphatic alcohols, such as resorcitol, quinitol, bis-(4-hydroxycyclohexyl)-methane, 2,2-bis-(4-hydroxycyclohexyl)-propane and 1,1-bis-(hydroxymethyl)-cyclohexane, and from alcohols with aromatic nuclei, such as N,N-bis-(2-hydroxyethyl)-aniline, p,p'-bis-(2-hydroxyethyl)-aniline and p,p'-bis-(2-hydroxyethylamino)-diphenylmethane. They can furthermore be obtained from mononuclear phenols, such as resorcinol and hydroquinone, and polynuclear phenols, such as bis-(4-hydroxyphenyl)-methane (bisphenol F), 4,4'-dihydrodiphenyl, 1,1,2,2-tetrakis-(4-hydroxyphenyl)-methane and 2,2-bis-(4-hydroxyphenyl)-propane (bisphenol A), and from novolaks formed by reaction of aldehydes, such as formaldehyde, acetyldehyde and benzaldehyde, with phenol or alkyl-substituted phenol, it being possible for the alkyl groups in each case to contain up to nine carbon atoms, such as 2-methylphenol and 4-tert.-butylphenol.

Poly-(N-glycidyl) compounds can also be used for the process according to the invention, for example N-glycidyl derivatives of amines, such as aniline, n-butylamine, bis-(4-aminophenyl)-methane and bis-(4-methylaminophenyl)-methane, triglycidyl isocyanurate and N,N'-diglycidyl derivatives of cyclic alkyleneureas, such as ethyleneurea and 1,3-propyleneurea, and of hydantoins, such as 5,5-dimethylhydantoin.

It is also possible to employ poly-(S-glycidyl) compounds, for example di-(S-glycidyl) derivatives of dithiols, such as ethane-1,2-dithiol and bis-(4-mercaptomethylphenyl)ether, but these are not preferred.

Glycidyl compounds in which the glycidyl groups are bonded to different hetero-atoms, for example p-(diglycidylamino)-phenyl glycidyl ethers, are also suitable.

The glycidyl ethers, in particular those of mononuclear phenols, are preferably employed in the process according to the invention.

Examples of suitable halogen-free organic solvents which can be employed in the process according to the invention are aliphatic hydrocarbons, such as pentane, hexane, heptane or octane, cycloaliphatic hydrocarbons, such as cyclohexane or cyclopentane, aromatic hydrocarbons, such as benzene, toluene or xylenes, aliphatic or cyclic ethers, such as diethyl ether, dioxane or tetrahydrofuran, and ketones, such as methyl ethyl ketone or methyl isobutyl ketone.

Sodium hydroxide solution is preferably used for treating the glycidyl compounds with aqueous alkali metal hydroxides. The treatment is preferably carried out in the temperature range from 60° to 130° C. by gradually adding the aqueous alkali metal hydroxide solution to the glycidyl compound dissolved in an organic solvent, with stirring. 20 to 90% by weight aqueous alkali metal hydroxide solutions are in general employed here, these preferably being added for the treatment of glycidyl ethers in amounts such that the excess is 100 to 170%, in particular 120 to 170%, of the theoretically required equivalent amount.

The excess is preferably 150–200% in the treatment of N-glycidyl compounds.

Depending on the temperature used and the concentration of the alkali metal hydroxide solution employed, the treatment lasts between about 10 minutes and about one hour. For example, if a 30% by weight sodium hydroxide solution is used, a treatment time of about half an hour is sufficient if treatment is carried out at about 80° C. After this treatment, the water is removed from the organic solution, preferably be means of azeotropic distillation.

The treatment time of the organic solution containing the glycidyl compound with moist cellulose containing up to 35% by weight of water, based on the dry weight of the cellulose, can vary within wide limits, and is in general at least 20 minutes, preferably ½ to 1 hour. The treatment with cellulose is preferably carried out in the temperature range from 30° to 90° C., in particular between 50° and 80° C., and is preferably carried out with continuous stirring of the organic solution.

The cellulose employed preferably contains up to 30% by weight of water and at least about 5% by weight, in particular at least about 10% by weight, of water.

The moist cellulose used is prepared by simply moistening commercially available cellulose with the corresponding amount of water. Either the fibrous cellulose, commercially available, for example, under the name Solka Floc from Brown, USA, or pulverulent cellulose, such as is commercially available, for example, under the name Arbocel® from Rettenmaier and Söhne, Germany, can be used as the cellulose.

After the cellulose has been filtered off, the glycidyl compounds are obtained by removing the organic solvent. As already mentioned, the glycidyl compounds purified by the process according to the invention are particularly suitable for applications in the electronics sector.

The amounts of hydrolysable chlorine and ionic chlorine quoted in the following examples are determined potentiometrically by the following method:

10 g of the glycidyl compound are dissolved in 100 ml of acetone. 1 ml of 0.001N aqueous NaCl solution, 1 ml of acetic acid and 2 ml of demineralised water are then added. Potentiometric determination of the chlorine content is carried out immediately using 0.001N silver nitrate solution in acetic acid.

The Cl determination method is repeated as a blank experiment—without the glycidyl compound. The actual chlorine content can be determined from the difference.

EXAMPLE 1

400 g of a cersol-novolak epoxy resin which has been prepared industrially from cresol-novolak and epichlorohydrin in the presence of sodium hydroxide solution and has an epoxide content of 4.62 equivalents/kg, a content of hydrolysable chlorine of 0.095% by weight and a viscosity of 2,750 mPa.s at 130° C. are dissolved completely in methyl isobutyl ketone (MIBK) at room temperature and the solution is heated to 85° C. 1.9 g of a 29.8% by weight aqueous sodium hydroxide solution are then added in the course of 30 minutes, with stirring. The solution is heated to 113° C., water being azeotropically removed from the solution, until the water content is less than 0.1% by weight. After cooling to 60° C., 4.6 g of water are added and the solution is stirred for 10 minutes. 35 g of moist cellulose (Arbocel ® 875) with a water content of 30% by weight are then added to the solution and the mixture is stirred for 30 minutes. The solution is then filtered using a 100 micron filter. The solvent is removed from the filtrate by means of vacuum distillation, the vacuum gradually being increased to 135° C./30 mbar. The resin is then stripped with water and subsequently with nitrogen gas for the purpose of removing all the volatile organic constituents. A cresol-novolak epoxide resin having an epoxide content of 4.62 equivalents/kg, a content of hydrolysable chlorine or 0.0028% by weight, a content of ionic chlorine of less than 0.0001% by weight and a viscosity of 3,060 mPa.s at 130° C. is obtained.

EXAMPLE 2

By the same procedure described in Example 1, 100 g of a tetra-(p-glycidyloxyphenyl)-ethane which has been prepared industrially from tetra-(p-hydroxyphenyl)-ethane and epichlorohydrin in the presence of sodium hydroxide solution and has an epoxide content of 4.78 equivalents/kg and a content of hydrolysable chlorine of 0.18% by weight are dissolved in MIBK and treated with 1.0 g of a 30% by weight aqueous sodium hydroxide solution and with 16 g of moist cellulose containing 30% by weight of water. Tetra(p-glycidyloxyphenyl)-ethane with an epoxide content of 4.80 equivalents/kg, a content of hydrolysable chlorine or 0.0063% by weight and a content of ionic chlorine of less than 0.0001% by weight is obtained.

EXAMPLE 3

By the procedure described in Example 1, 100 g of a bisphenol A diglycidyl ether which has been prepared industrially from bisphenol A and epichlorohydrin in the presence of sodium hydroxide solution and has an epoxide content of 5.24 equivalents/kg, a content of hydrolysable chlorine of 0.30% by weight and a viscosity of 13,400 mPa.s at 25° C. are dissolved in MIBK and treated with 1.3 g of a 30% by weight aqueous sodium hydroxide solution and with 20 g of moist cellulose containing 30% by weight of water. The resin solution is filtered through a 10 micron filter and worked up as in Example 1.

Bisphenol A diglycidyl ether with an epoxide content of 5.28 equivalents/kg, a content of hydrolysable chlorine of 0.0011% by weight and a content of ionic chlorine of less than 0.0001% by weight is obtained.

EXAMPLE 4

400 g of the cresol-novolak epoxy resin used in Example 1 are dissolved in 600 g of toluene and heated to 85° C. Then 2.41 g of a 30.24% by weight aqueous sodium hydroxide solution are added in the course of 15 minutes under strong stirring. The solution is heated to 112° C., water being azeotropically removed from the solution, until the water content is less than 0.03% by weight. After cooling to 65° C., 5.84 g of water are added and the solution is stirred for 5 minutes. 34.7 g of wetted cellulose containing 1% by weight of water are then added to the solution and the mixture is stirred for 15 minutes.

The resulting solution is filtered using a 100 micron filter and the solvent is removed by vacuum distillation rising the temperature gradually to 135° C. and bringing the vacuum down to 220 mbar. Then the resin is stripped with water to eliminate all kinds of organic volatiles. A final stripping with nitrogen gas allows to obtain a cresol-novolak epoxy resin having a epoxy content of 4.65 equivalents/kg, a content of hydrolysable chlorine of 0.0035% by weight, a content of ionic chlorine of 0.0001% by weight and a viscosity of 3450 mPa.s at 130° C.

What is claimed is:

1. A process for reducing the content of hydrolysable chlorine in a glycidyl compound by after-treatment of the glycidyl compound with an alkali metal hydroxide, which comprises treating the glycidyl compound, dissolved in a halogen-free organic solvent, with an equivalent excess of an aqueous alkali metal hydroxide solution at elevated temperature, the excess being 100 to 200% of the equivalent amount theoretically required for complete dehydrochlorination of the hydrolysable chlorine, removing the water from the organic solution by azeotropic distillation, treating the organic solution with 5 to 500 times the amount, based on the amount of alkali metal hydroxide employed, of moist cellulose containing 1% to 35% by weight of water at elevated temperature and, after filtration, isolating the glycidyl compound from the organic solution.

2. The process according to claim 1, wherein a glycidyl ether is employed as the glycidyl compound.

3. The process according to claim 1, wherein a glycidyl ether of a polynuclear phenol is employed as the glycidyl compound.

4. The process according to claim 1, wherein the treatment of the glycidyl compound with alkali metal hydroxide is carried out in the temperature range from 60° to 130° C.

5. The process according to claim 3, wherein the excess of alkali metal hydroxide is 100 to 170%, of the theoretically required equivalent amount.

6. The process according to claim 1, wherein the moist cellulose contains 5% to 30% by weight of water, based on the dry weight of the cellulose.

7. The process according to claim 1, wherein the treatment of the organic solution with cellulose is carried out in the temperature range from 30° to 90° C.

8. The process according to claim 1, wherein the treatment of the organic solution with cellulose is carried out in the temperature range from 50° to 80° C.

9. The process according to claim 1, wherein 10 to 100 times the amount of cellulose is employed.

10. The process according to claim 1, wherein pulverulent cellulose is employed.

11. A process according to claim 5 wherein the excess of alkali metal hydroxide is 120 to 170% of the theoretically required equivalent amount.

* * * * *